(12) United States Patent
Fornasiero

(10) Patent No.: US 8,050,547 B2
(45) Date of Patent: Nov. 1, 2011

(54) DEVICE AND PROCESS FOR UNIFORMLY LIGHTING AN OPERATING AREA

(75) Inventor: Livio Fornasiero, Hamburg (DE)

(73) Assignee: Dräger Medical GmbH, Lübeck (DE)

( * ) Notice: Subject to any disclaimer, the term of this patent is extended or adjusted under 35 U.S.C. 154(b) by 233 days.

(21) Appl. No.: 12/418,784

(22) Filed: Apr. 6, 2009

(65) Prior Publication Data

US 2009/0261759 A1  Oct. 22, 2009

(30) Foreign Application Priority Data

Apr. 17, 2008 (DE) .......................... 10 2008 019 191

(51) Int. Cl.
*G03B 15/02* (2006.01)
(52) U.S. Cl. ................................. 396/4; 362/3; 362/804
(58) Field of Classification Search .......... 396/4; 362/3, 362/804
See application file for complete search history.

(56) References Cited

U.S. PATENT DOCUMENTS

| 4,288,844 | A  * | 9/1981  | Fisher et al. ................... 362/33 |
| 6,270,228 | B1 * | 8/2001  | Axen et al. ....................... 362/3 |
| 6,351,678 | B1 * | 2/2002  | Borders ............................ 700/83 |
| 6,402,351 | B1 * | 6/2002  | Borders et al. ................ 362/395 |
| 6,880,957 | B2   | 4/2005  | Walters |
| 7,231,060 | B2 * | 6/2007  | Dowling et al. .............. 382/100 |
| 7,234,814 | B2 * | 6/2007  | Morita et al. ................. 351/203 |
| 7,311,410 | B2 * | 12/2007 | Marka .............................. 362/33 |
| 7,465,065 | B2 * | 12/2008 | Marka ............................ 362/232 |
| 2003/0164953 | A1 * | 9/2003  | Bauch et al. .................. 356/611 |
| 2004/0129860 | A1 * | 7/2004  | Thibaud et al. ............... 250/205 |
| 2006/0061248 | A1 * | 3/2006  | Cok et al. ....................... 313/110 |
| 2008/0247163 | A1 * | 10/2008 | Chen ............................. 362/237 |

FOREIGN PATENT DOCUMENTS

| DE | 202005021111 |    | 5/2007 |
| EP | 1 433 998 |    | 6/2004 |
| EP | 1 568 935 | A1 | 8/2005 |
| EP | 1 728 482 | A1 | 12/2006 |
| EP | 1 785 665 |    | 5/2007 |

* cited by examiner

*Primary Examiner* — W. B. Perkey
*Assistant Examiner* — Linda Smith
(74) *Attorney, Agent, or Firm* — McGlew and Tuttle, P.C.

(57) ABSTRACT

A device and a process are provided for uniformly lighting an operating area for performing the lighting of an operating area (2) of a bed (30) by means of a lighting unit (3) such that a selected lighting field (13) is lighted uniformly. The image signals of a camera (7) are sent to an image processing unit (17), in which the image signals are analyzed and the individual lighting elements (6) are switched via the control unit (18). A lighting situation is acquired in the process for initializing and operating this lighting system and a lighting field (13) of interest is selected. The image signals are analyzed during the operation and sent to the control unit (18) in order to switch the lighting elements (6) such that uniform lighting is obtained in the first lighting field (13).

22 Claims, 8 Drawing Sheets

DEVICE AND PROCESS FOR UNIFORMLY LIGHTING AN OPERATING AREA

CROSS REFERENCE TO RELATED APPLICATIONS

This application claims the benefit of priority under 35 U.S.C. §119 of German Patent Application DE 10 2008 019 191.4 filed Apr. 17, 2008, the entire contents of which are incorporated herein by reference.

FIELD OF THE INVENTION

The present invention pertains to a device comprising a lighting fixture for an operating room with a lighting unit, in which a plurality of lighting elements with at least one light source are arranged, a camera for imaging, with an image processing system, with a control unit for actuating the lighting elements, with a display unit and with an operating unit. Furthermore, the present invention pertains to a process for lighting preselected lighting fields of an operating area.

BACKGROUND OF THE INVENTION

A combination of imaging system, image processing system and operating area is known from DE 20 2005 021111 U1.

EP 1785665 A1 describes an operating area with an actuating means of groups of lighting means, wherein the lighting means can be controlled in terms of luminosity in a plurality of zones separately from one another.

EP 1433998 B1 describes a lighting fixture for an operating room with a control unit, imaging and processing system, in which it is possible to determine shadow zones above an operating area by imaging and by an analysis unit. After determination of the shadow zone, the light distribution is changed by means of the control unit in order to reduce the shadow effect.

The drawback of this arrangement of cameras and lighting fixtures for the operating room is that it is necessary to divide the lighted operating area into checkerboard-like partial areas and that a certain, defined and known group of a number of lighting means is permanently assigned to each of these partial areas.

SUMMARY OF THE INVENTION

An object of the present invention is therefore to provide a device with an operating area and a process for operating same in such a way that uniform lighting of the operating area is guaranteed.

The device according to the present invention comprises a lighting fixture for a lighting means of an operating room. The lighting means comprises a plurality of individual lighting elements. In a preferred form, these are LED lighting elements. The device comprises, furthermore, at least one camera, which is aligned stationarily in relation to the operating area; at least one central lighting unit or a group of centrally positioned lighting means; an image processing system; a display unit; an operating unit, and a control unit for controlling the plurality of lighting elements. The camera is arranged in a fixed relationship to an operating area belonging to it, which is located in the area covered by the camera. The lighting unit is equipped with a plurality of lighting elements such that the operating area can be lighted in a plurality of lighting zones.

The process for operating a lighting system for uniformly lighting a lighting field begins with the switching on of the plurality of lighting elements sequentially one after another and with the acquisition of an image by at least one first camera, an image being acquired for every single switch-on event, recorded and stored in a first data field. The data image acquired by the at least first camera is subsequently analyzed in a continuous sequence and compared with the first data field. The actuation parameters of a first parameter field are thereupon adjusted and the control unit continuously controls the individual lighting elements of the lighting unit according to the first parameter field.

A sequence of eleven steps specifically illustrates the process according to the present invention for operating a lighting system for uniformly lighting a lighting field. The process takes the following course:

a) All lighting elements of the lighting unit are switched on simultaneously by the control unit in a first step;
b) an image of the operating area is acquired by at least one first camera and displayed on the display unit in a second step;
c) at least one first lighting field of interest with a corresponding defined brightness distribution is set by means of the operating unit in a third step;
d) all lighting elements of the lighting unit are switched off by the control unit in a fourth step and each one of the plurality of lighting elements is switched on one after another in a sequence and an image is acquired, recorded and stored in a first data field for every single switch-on event of every single lighting element by at least one first camera;
e) the first data field is analyzed in a fifth step to determine whether the at least first camera was hidden during the imaging;
f) the first data field is analyzed in a sixth step and the parameters for actuating the plurality of lighting elements are determined and stored in a first parameter field;
g) the individual lighting elements are switched by means of the control unit in a seventh step and a control view of the lighting is outputted on the display unit;
h) the actuation of the plurality of lighting elements is confirmed by means of the operating unit in an eighth step, the initialization is terminated and operation is started;
i) a polling is carried out in a ninth step to execute the first mode of operation for uniform lighting, and the first mode of operation is continued;
j) the data image acquired by the at least first camera is analyzed in a tenth step in a continuous sequence and compared with the first data field, and the actuating parameters of the first parameter field are adjusted; and
k) the actuation of the individual lighting elements of the lighting unit is performed in an eleventh step according to the first parameter field and the first mode of operation is continued without interruption with return to the ninth step.

In a special embodiment of the process, a polling is provided in the ninth step to terminate the first mode of operation with simultaneous lighting, as well as a polling is provided for switching over into at least a second mode of operation, wherein the second mode of operation may be designed as a mode with maximum luminosity of all lighting elements, as a mode based on an average brightness distribution of all lighting elements according to the first parameter field, or as a mode of manually preset luminosity of all lighting elements.

In another preferred embodiment of the process, a first lighting field of interest and at least one second lighting field are set by means of the operating unit in the third step.

In an expanded embodiment of the process, a return to the first step and hence a restart of initialization can take place following the fifth step, if the at least first camera is hidden, as a result of the analysis of the data in the first data field, and the user is informed of the reason for the return in the form of a message. The process according to the present invention comprises an arrangement of at least one lighting unit for lighting an operating area, wherein each lighting unit comprises a plurality of lighting elements, and comprises an image recording of the lighting situation by means of at least one stationarily arranged first camera. The lighting situation is displayed for the user on a display unit. The user defines by means of an operating unit the lighting fields in the operating area in which uniform lighting must be guaranteed. The geometric shape of the lighting fields may be as desired, the extension of the lighting field being smaller than the operating area.

Exemplary shapes of the lighting field are circles, ellipses, square, trapezoidal and rectangular tetragonal shapes, honeycomb shapes with five, six or seven corners. Sequential switching on of all lighting elements is performed in the next step by the actuating unit, and an image is recorded by the camera for each switch-on event of every single lighting element.

The images recorded by the camera are stored in a first data set. The percentage of an image segment of the operating area and of the defined lighting field for which an individual lighting element is responsible is calculated in the next step. A two-dimensional data field of lighting values of the operating area with the subset of a data field, which describes the defined lighting field, is obtained from this.

After this initialization, the control unit actuates individual lighting elements, so that uniform lighting of the lighting field defined by the user is guaranteed.

The camera detects the lighting situation of the operating area and of the defined lighting field. The image signals are sent to the image processing unit, which analyzes the lighting for uniformity. The uniformity of lighting can be determined by a comparison with a preset limit value. Mathematical methods make it additionally possible to determine the conditions of the luminosities in relation to one another, to a preset limit value or to a mean value of the luminosities. Thus, the deviation of the brightness distribution of a group of measured values in relation to the stored or preselected desired values or even the brightness distribution of the measured values within the group of measured values in relation to one another is determined by the analysis by means of the least-squares method.

The use of the least-squares method represents a known image analysis method here; other image analysis methods, such as an analysis of the frequency components in the form of a distribution analysis (histogram analysis) with preceding frequency transformation (FFT), the targeted analysis of certain dot marks in a first lighting field represent alternative and additionally applicable methods for image analysis. The inclusion of past image data for a trend analysis of the change in brightness and also of a brightness shift from one group of image segments to another group of image segments makes it possible in a special embodiment to recognize both a temporary shadowing of individual areas of the first lighting field and dynamic shadow processes caused by motion. The results of the analysis are stored in a first parameter field, and the luminosity of individual lighting elements is controlled in the control circuit with the control unit such that the lowest possible relative deviation of the brightness distribution of the lighting detected with the camera remains within the lighting field in relation to stored or preselected desired values of the brightness distribution or also within one group of image segments in the lighting field.

In a preferred embodiment, means for pulsed switchover are provided and the lighting elements are designed such that switchover of the lighting elements can take place at a switchover frequency above the flicker fusion frequency of 80 Hz so rapidly that the switchover processes cannot be perceived by the human eye as disturbing processes in the brightness of the emitted light. Suitable lighting elements for rapid switchover are light-emitting diodes.

At least two cameras, whose acquisition areas overlap and which are arranged in a fixed relationship to the operating area, are present in a preferred embodiment.

The control unit is designed in an alternative variant to control a number of at least two lighting units on the basis of the image analysis. The first and/or second camera is part of a central lighting unit in another preferred embodiment.

The lighting unit connected to the camera is arranged in a special embodiment stationarily on the ceiling of the operating room directly centrally above the operating area, whereas other additional lighting units are arranged movably and pivotably about the central lighting unit, and these additional lighting units are also included in the lighting control.

A special variant of the process is designed such that a special mode of operation is provided, in which low priority can be set for uniform lighting of the lighting field in favor of higher intensity of lighting of the operating area.

An exemplary embodiment of the present invention will be explained in more detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
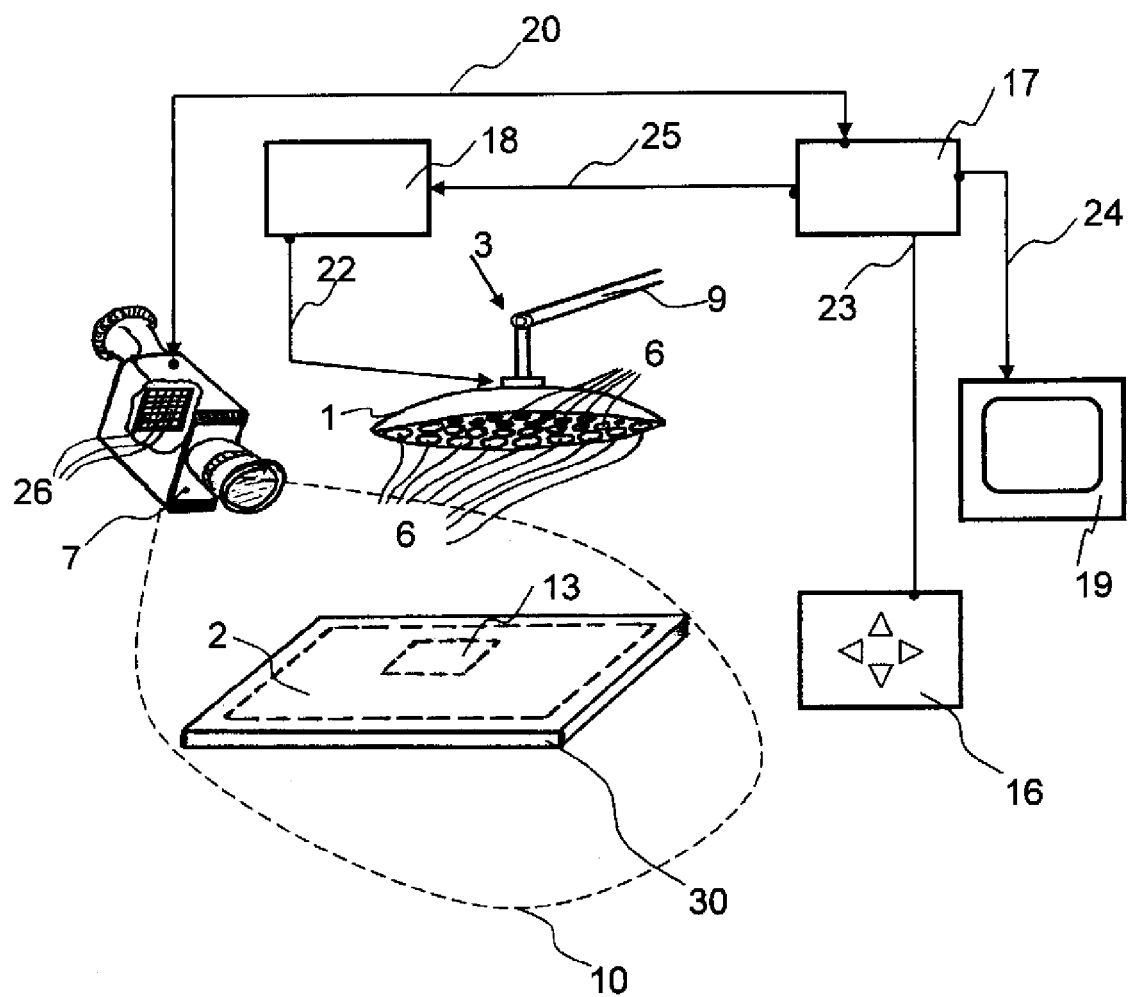
FIG. 1 is a schematic view showing an arrangement comprising an operating area, a lighting unit, a display unit, an operating unit and a control unit as well as a first camera.

Referring to the drawings in particular, FIG. 1 shows a first lighting unit 3 according to the present invention as it is used, for example, in operating rooms of hospitals, comprising a lighting fixture housing 1, with a plurality of lighting elements 6. The lighting fixture housing 1 is fastened via a suspension 9 to a ceiling, not shown, of the operating room. Also shown is a first camera 7 with a first acquisition area 10. This first acquisition area 10 is designed such that it is suitable for covering the operating area 2 of a bed 30. The first lighting unit 3 is connected via a first control line 22 to a first control unit 18.

The data acquired by the camera 7 as a field of image segments 26 are sent via a first signal and switching line 20 to an image processing unit 17. The image processing unit 17 is connected to an operating unit 16 by means of a second control line 23 and to a display unit 19 by means of a third control line 24 as well as to the control unit 18 by means of a fourth control line 25.

The control line 18 is designed to individually control the luminosity of the individual lighting elements 6.

Figure 2:
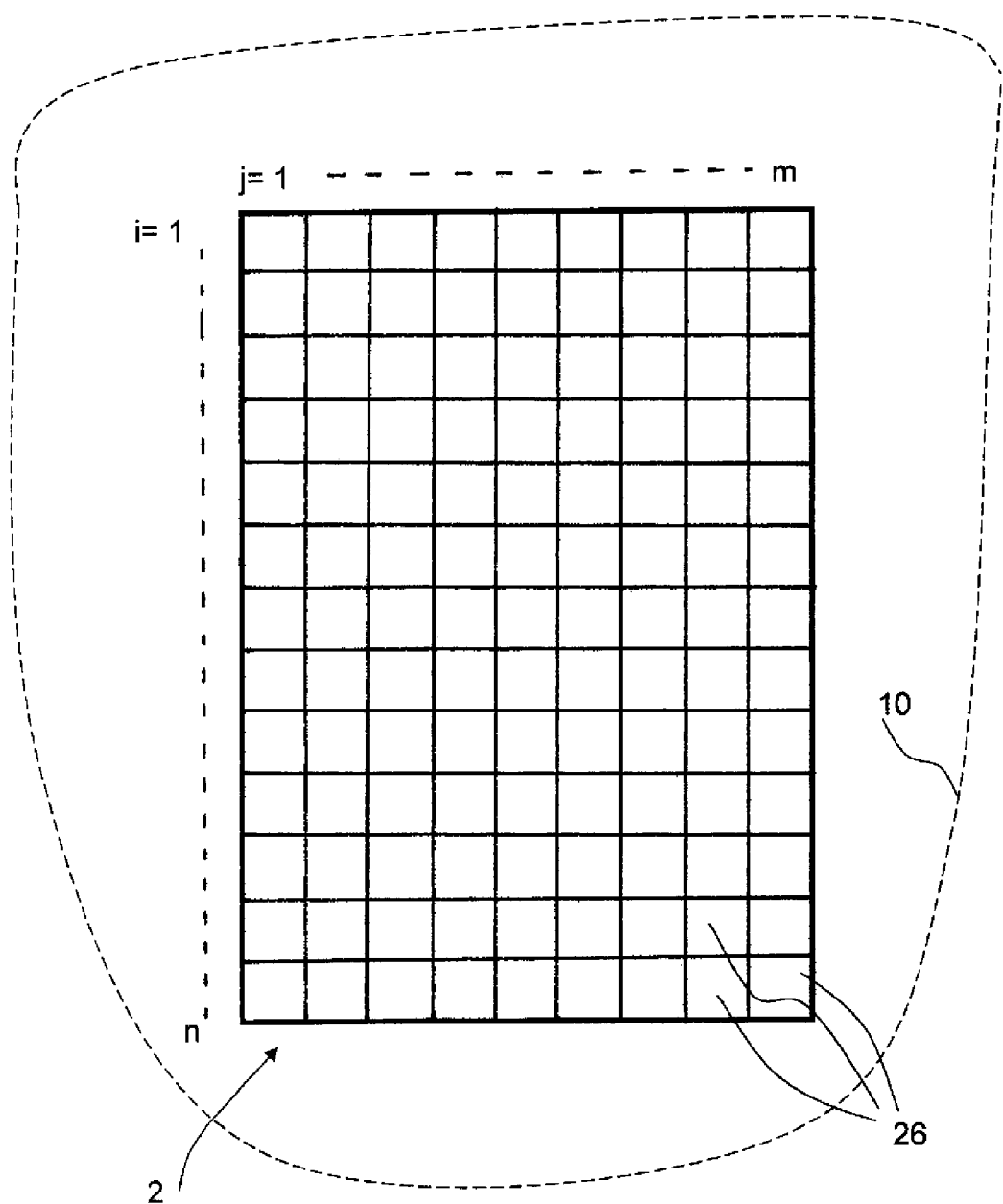
FIG. 2 is a view showing the division of the imaging of the operating area into image segments and a first acquisition area of a first camera.

FIG. 2 shows an image of the operating area 2 with image segments 26 of a first acquisition area 10 of the first camera 7, which said image segments are acquired by the first camera 7. The image segments 26 are indexed in one orientation by means of variable i ranging from 1 to n, and in an orientation at right angles thereto by means of variable j ranging from 1 to m in a first data field 57 (see FIG. 8). The image segments determined by the indices of the first data field 57 determine a horizontal and vertical resolution of a camera image, the product of the horizontal and vertical resolutions being usually expressed as resolution in pixels in the description of the technical features of a digitally recording camera.

Figure 3:
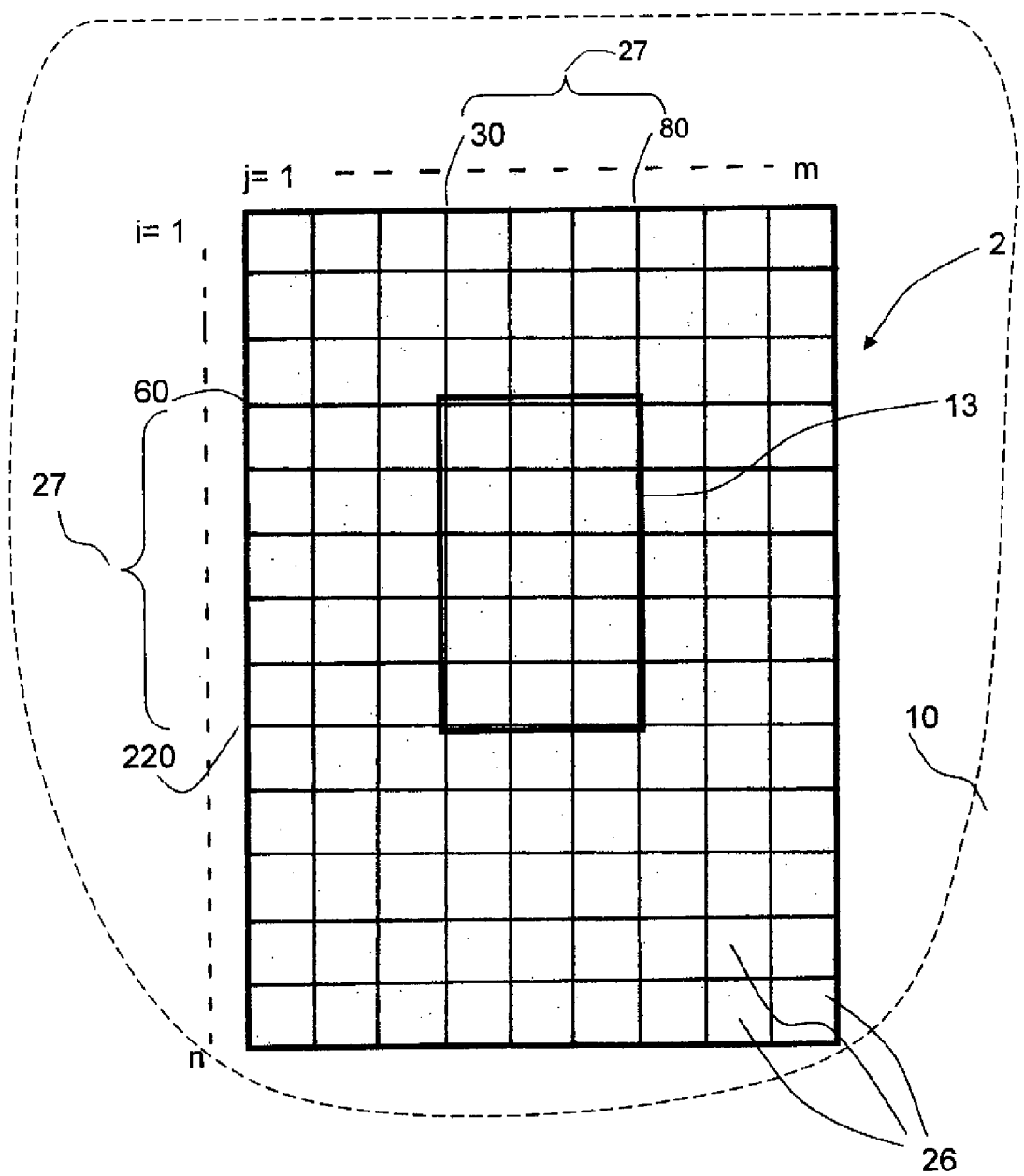
FIG. 3 is a view showing the division of the operating area in connection with a defined lighting field.

FIG. 3 shows an image of the operating area 2 with the image segments 26 and with a first acquisition area 10 of the first camera 7. A first lighting field 13 is represented in the image of the operating area 2 with the corresponding subset of a first group of image segments 26, which is described in position and size in the operating area 2 with a first set of coordinates 27 by means of the field indices i=60 to 200 and j=30 to 80.

Figure 4:
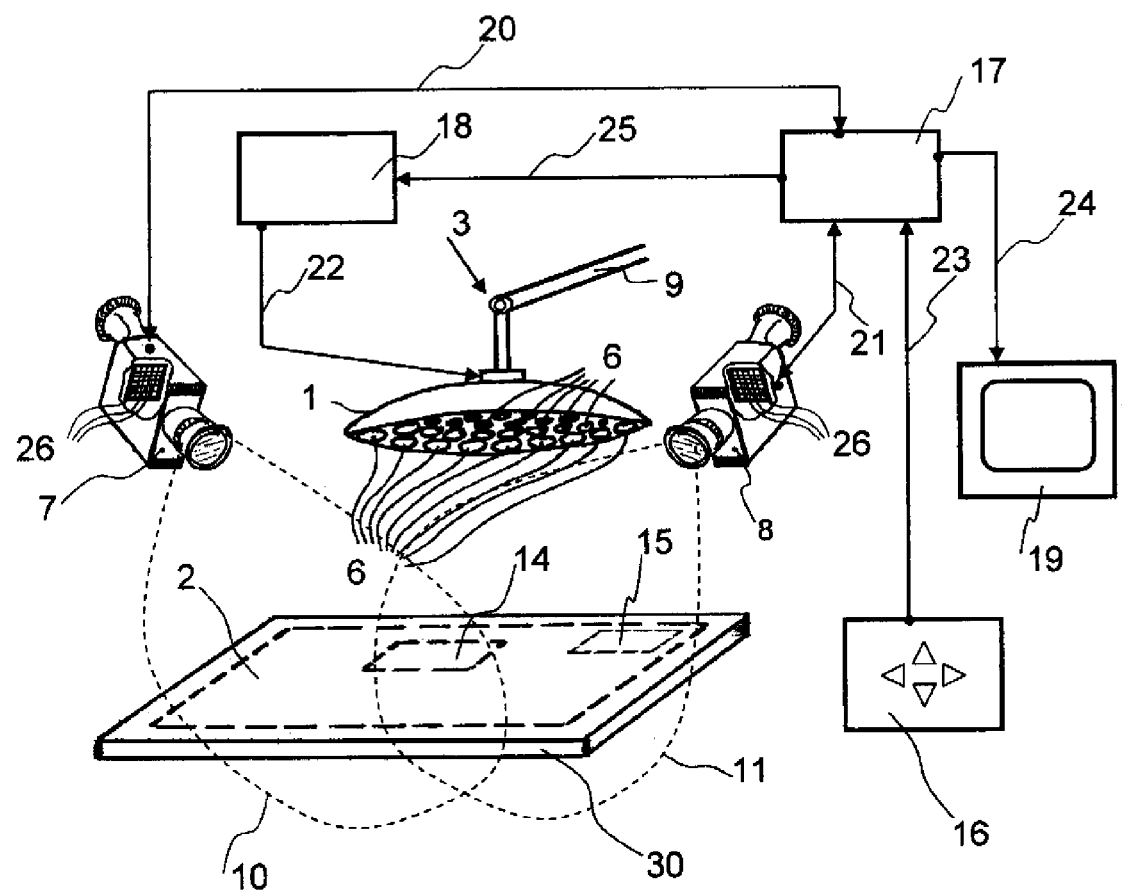
FIG. 4 is a schematic view showing an arrangement comprising an operating area, a lighting unit, a display unit, an operating unit and a control unit as well as two cameras with two overlapping acquisition areas.

Besides the components from FIG. 1, FIG. 4 shows a second camera 8 with a second acquisition area 11. The second camera 8 is connected to the image processing unit 17 by means of a second signal and switching line 21. Components that are identical to those in FIG. 1 are designated by the same reference numbers.

Figure 5:
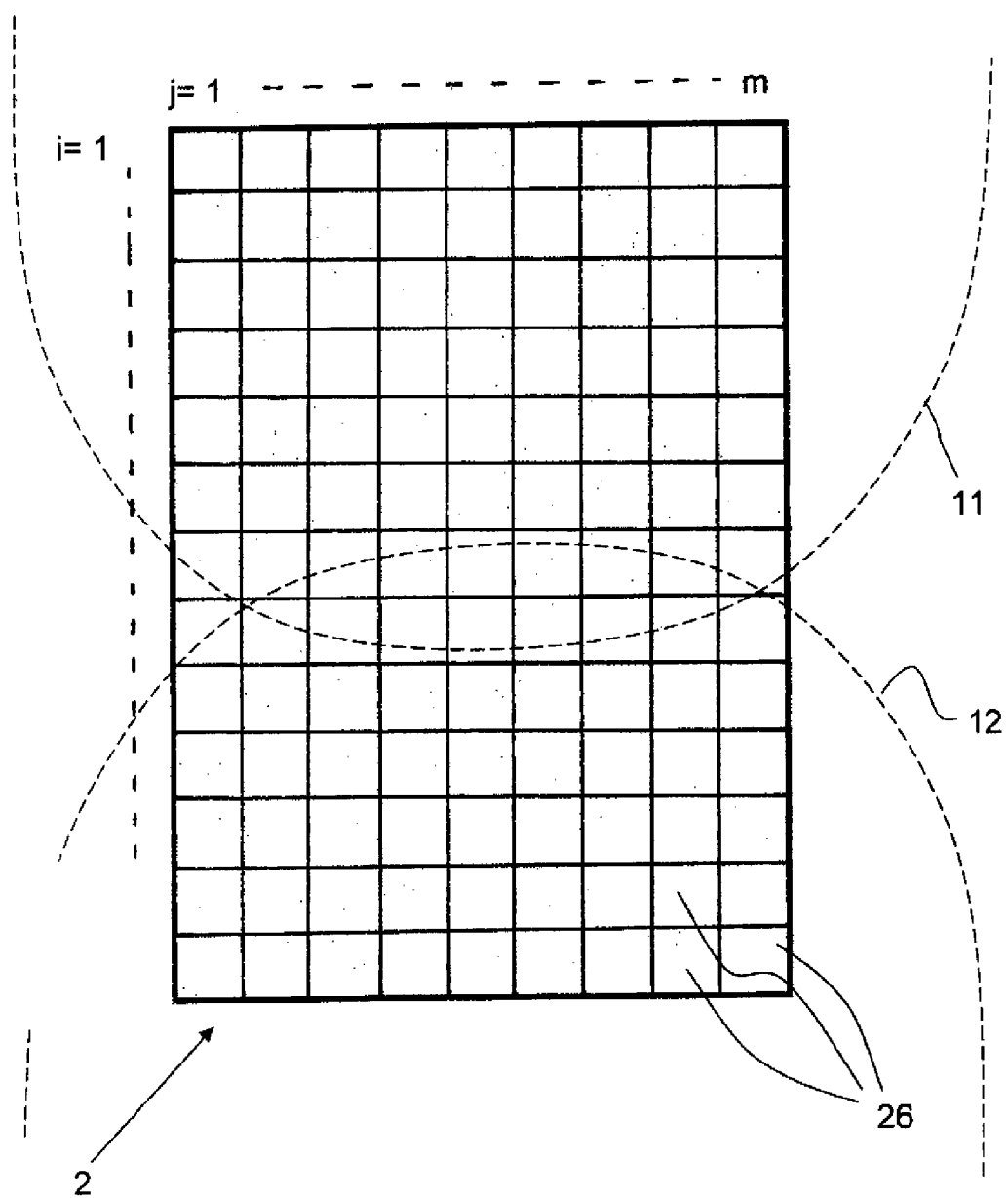
FIG. 5 is a view showing the division of the image of the operating area into image segments and a first acquisition area and a second acquisition area of two cameras.

FIG. 5 shows an image of the operating area 2 with the indexed image segments 26 and with a second acquisition area 11 of the second camera 8, as well as with an alternative third acquisition area 12 of the first camera 7.

Figure 6:
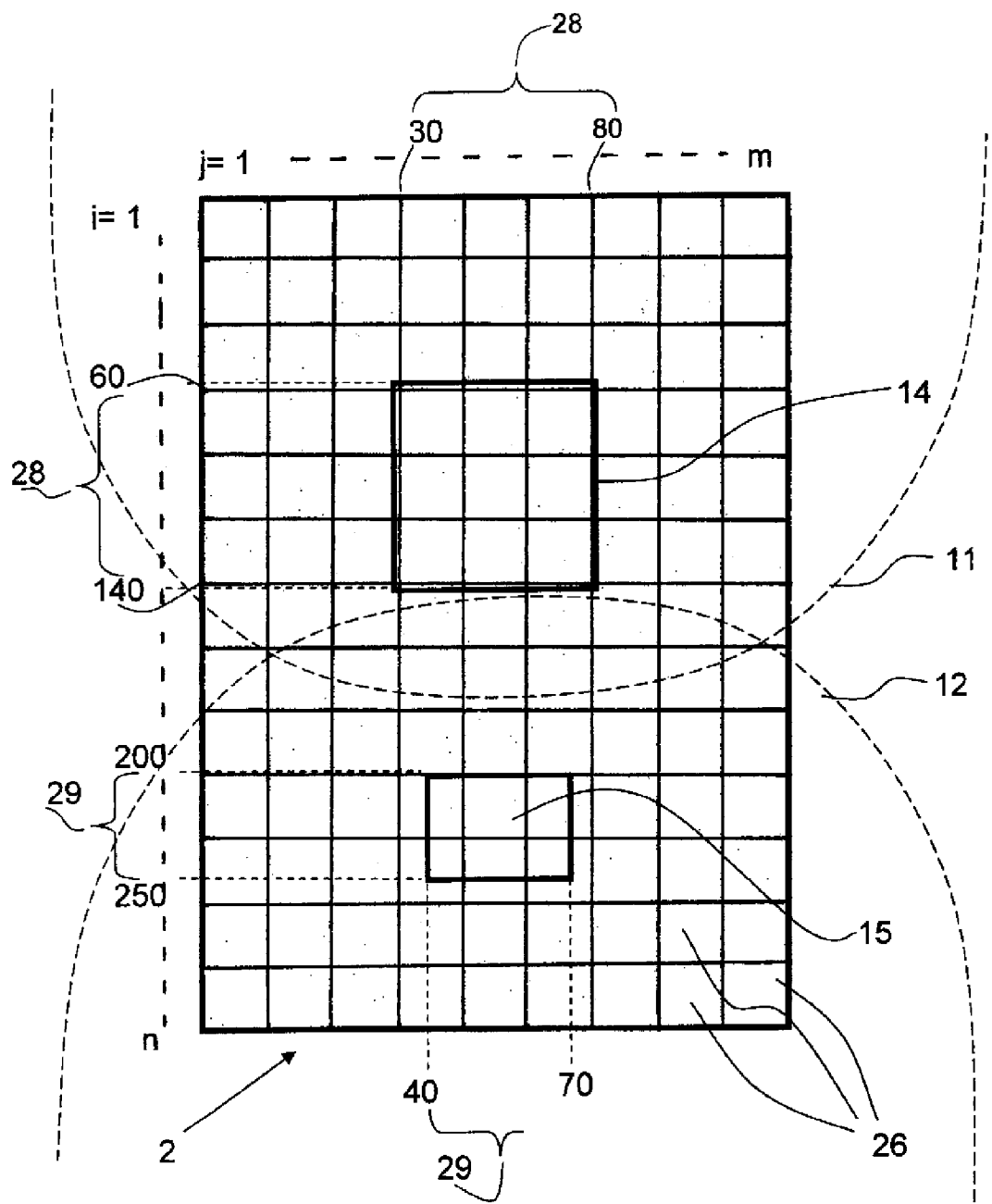
FIG. 6 is a view showing the division of the operating area in connection with two defined lighting fields.

FIG. 6 shows an image of the operating area 2 with the image segments 26 and with a second acquisition area 11 of the second camera 8 as well as with an alternative third acquisition area 12 of the first camera 7. A second lighting field 14 with the corresponding subset of a second group of image segments 26, which lighting field is described in terms of its position and size in the operating area 2 with a second set of coordinates 28 by means of the field indices i=60 to 140 and j=30 to 80. A third lighting field 15 is described with a third set of coordinates 29 by means of the field indices i=200 to 250 and j=40 to 70.

Figure 7:
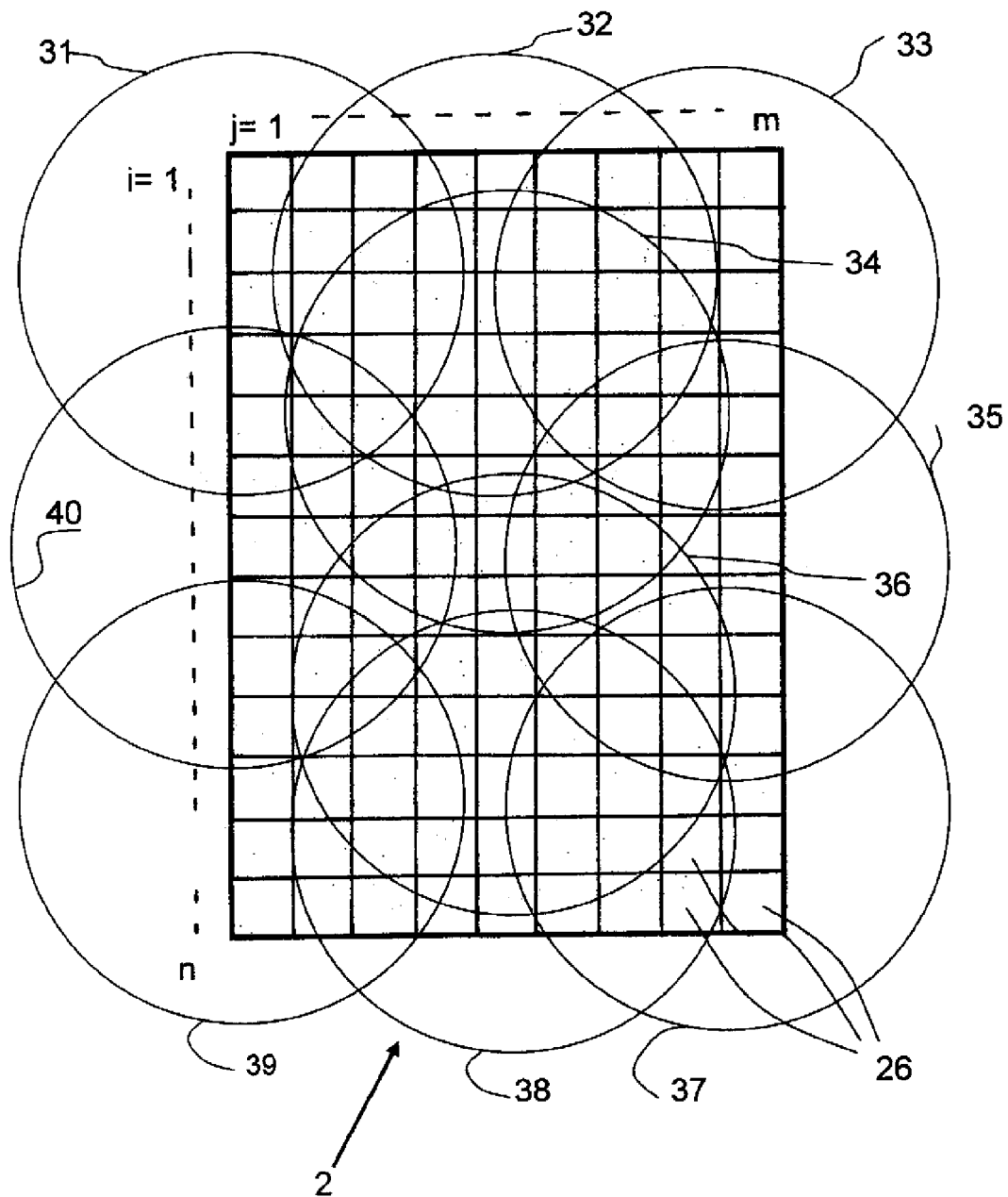
FIG. 7 is a view showing the division of the image of the operating area into image segments together with the lighting zones of individual lighting elements.

FIG. 7 shows an image of the operating area 2 according to FIG. 2 with the image segments 26 and with an exemplary number of 10 lighting zones 31, 32, 33, 34, 35, 36, 37, 38, 39, 40 shown. The lighting zones arise from a number of 10 switched-on lighting elements 6 of the first lighting unit 3 in the lighting fixture housing 1.

Figure 8:
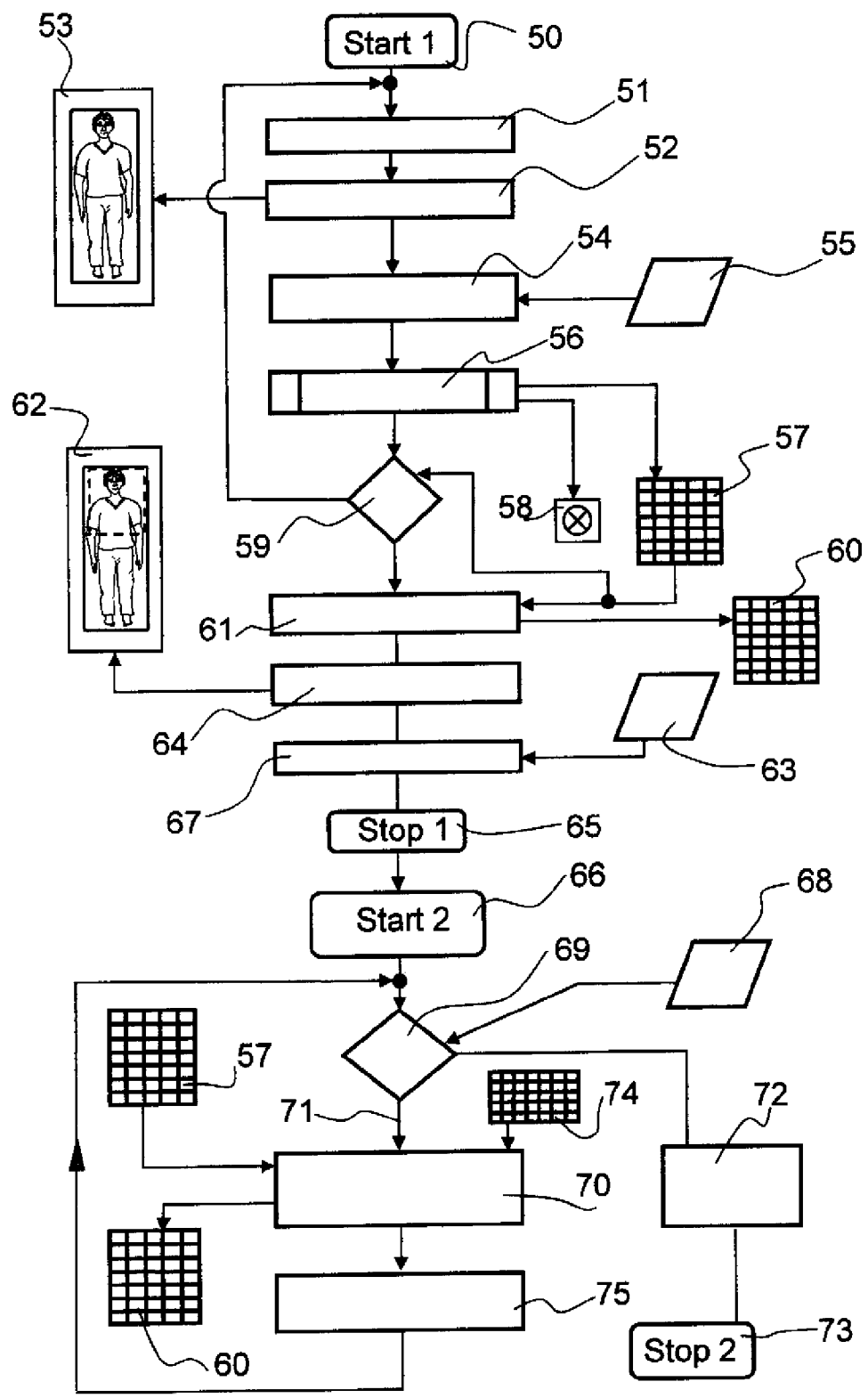
FIG. 8 is a view showing a flow chart for initializing and activating a mode of operation for uniform lighting.

The process of uniformly lighting a lighting field is shown in FIG. 8 as a flow chart and begins after the start 50 in a first step 51 with the simultaneous switching on of all lighting elements 6 in a first lighting unit 3 by the control unit 18, the lighting elements 6 of the first lighting unit 3 emitting the light into the lighting zones 31, 32, 33, 34, 35, 36, 37, 38, 39, 40. An image of the operating area 2 is acquired by the first camera in a second step 52 and displayed on the display 19 as a first lighting view 53. In a third step 54, the user sets the first lighting field 13 of interest with a corresponding, defined brightness distribution in a first operation 55 by means of the operating unit 16. All lighting elements 6 are at first switched off in a fourth step 56 and each one of the plurality of lighting elements 6 is switched on one after another in an initialization routine, and an image is acquired, recorded and stored in a first data field 57 by the first camera 7 for every single switch-on event 58 of an individual lighting element 6. The first data field 57 is analyzed in a fifth step 59 by means of the image processing unit 17 to determine whether the first camera 7 was hidden during the image processing. If the first camera 7 was hidden, the process returns to the beginning of initialization in the first step 51 and the user is informed of the unsuccessful initialization via the display unit 19. The first data field 57 is analyzed in a sixth step 61 by means of the image processing unit 17 and the actuation parameters for actuating the plurality of lighting elements 6 for achieving uniform lighting in the first lighting field 13 are determined and stored in a first parameter field 60. The individual lighting elements 6 are switched by means of the control unit 18 in a seventh step 64 corresponding to the determined actuation parameters of the first parameter field 60, and the switched lighting zones 31, 32, 33, 34, 35, 36, 37, 38, 39, 40 bring about uniform lighting in the first lighting field 13. Furthermore, a control view 62 of the lighting is outputted on the display unit 19 in this seventh step 64. Initialization is concluded and brought to the end 65 in an eighth step 67 with a second operation 63 as a confirmation of the shown control view 62 of the lighting by the user.

The process for uniform lighting is then continued with the start 66. The user is polled in a ninth step 69 to determine whether he would like to activate the first mode of operation 71 for uniformly lighting the first lighting field 13 or whether he would like to activate a second mode of operation 72 for lighting. If the user selects the first mode of operation for uniformly lighting 71 the first lighting field 13 in a third operation 68 by means of the operating unit 16, the image data 74 currently being acquired by the first camera 7 are analyzed in a continuous sequence in the tenth step 70 and compared with the first data field 57, and the actuation parameters of the first parameter field 60 are adjusted. The individual lighting elements 6 of the first lighting unit 3 are actuated in an eleventh step 75 corresponding to the determined actuation parameters of the first parameter field 60. The process is returned after the eleventh step 75 to the ninth step 69 and remains in a repeating permanent loop, which can be brought to an end 73 by the user by jumping into the ninth step 69. In the third operation 69, the user has, alternatively to the first mode of operation 71, the choice of switching off the first mode of operation 71 and to switch over into a second mode of operation 72 for lighting the first operating area 2. The second mode of operation 72 may be a mode with maximum luminosity of all lighting elements 6 or a mode based on an average brightness distribution of all lighting elements 6 according to the first parameter field 60 or a mode in which the luminosities of all lighting elements are preset manually.

While specific embodiments of the invention have been shown and described in detail to illustrate the application of the principles of the invention, it will be understood that the invention may be embodied otherwise without departing from such principles.

What is claimed is:

1. A device for uniformly lighting at least one lighting field, the device comprising:
- a lighting fixture housing;
- a lighting unit with a plurality of lighting elements accommodated in said lighting fixture housing, said plurality of lighting elements providing at least one lighting field area as output;
- a camera having a camera acquisition area, said camera providing data relating to image segments of said at least one lighting field area as output;
- a control unit for providing actuating signals for actuating said lighting elements with data acquired by said camera in said camera acquisition area as said image segments;
- an image processing unit receiving said output of said camera, said image processing unit determining parameters of said image segments to light the at least one lighting field based on said data, wherein said control unit adjusts the actuating signals, for the plurality of lighting elements, to reduce the differences in the luminosities of the image segments based on said parameters of said image segments determined by said image processing unit
- an operating unit;
- a display unit, wherein:
  - said control unit switches on all lighting elements of the lighting unit simultaneously;
  - said camera acquires an image of the operating area, said image being displayed on said display unit;
  - said operating unit sets at least one lighting field of interest with a corresponding brightness distribution;
  - said control unit switches off all lighting elements and said control unit switches on each one of the plurality of lighting elements one after another in a sequence and said camera acquires an image for every single lighting element and stored in a first data field;
  - said image processing unit analyzes the first data field to determine if said camera was hiding from view;
  - said image processing unit further analyzes the first data field such that said image processing unit determines the parameters for actuating the plurality of lighting elements, said parameters being stored in a first parameter field;
  - said control unit switches the individual lighting elements and a control view of the lighting is provided as output on the display unit;
  - said operating unit confirms the actuation of the plurality of lighting elements, wherein initialization is terminated and operation of said lighting element is started;
  - a polling is performed via said operating unit to execute the first mode of operation for uniform lighting and the first mode of operation is continued;
  - said image processing unit analyzes the data image acquired by said camera in a continuous sequence and said image processing unit compares the first data field and said image processing unit adjusting the actuation parameters of the first parameter field; and
  - the actuation by the control unit of the individual lighting elements of the lighting unit is performed according to the first parameter field and the first mode of operation is continued without interruption with a return to said polling.

2. A device in accordance with claim 1, further comprising at least one additional camera having an additional camera acquisition area, said additional camera being connected to said image processing unit and wherein said additional camera acquisition area overlaps said camera acquisition area in an operating area.

3. A device in accordance with claim 1, wherein the at least one lighting field comprises at least two lighting fields illuminated by said lighting elements actuated by said control unit via a control line.

4. A device in accordance with claim 1, wherein said camera is integrated in said lighting fixture housing.

5. A device in accordance with claim 1, wherein said camera is aligned stationarily in relation to an operating area.

6. A device in accordance with claim 1, further comprising:
- an additional lighting unit, with a plurality of lighting elements, is connected to said control unit in addition to said lighting unit, said additional lighting unit being controlled on the basis of the parameters of the image processing unit.

7. A device in accordance with claim 1, wherein the lighting elements comprise light-emitting diodes.

8. A device in accordance with claim 1, further comprising means for a pulsed switchover of the lighting elements.

9. A device in accordance with claim 1, wherein said control unit adjusts the actuating signals of a control line for said lighting elements such that differences between luminosities of said image segments of the at least first lighting field is below a preset limit value.

10. A device in accordance with claim 6, wherein the at least additional lighting unit comprises a movable and pivotable unit.

11. A process for operating a lighting system for uniformly lighting a lighting field, the process comprising the steps of:
- providing a plurality of lighting elements;
- switching the lighting elements on one after another in a sequence to provide a plurality of switch-on events;
- acquiring an image with at least one camera for each of said switch-on events of every single lighting element;
- storing each acquired image in a first data field;
- in a continuous sequence analyzing a data image acquired by the at least one camera and comparing the data image acquired with the first data field;
- providing a first parameter field;
- continuously adjusting actuation parameters of the first parameter field; and
- continuously adjusting individual lighting elements and the control unit continuously actuates the lighting unit according to the first parameter field, wherein:
  - a) all lighting elements of the lighting unit are switched on simultaneously by the control unit in a step;
  - b) an image of the operating area is acquired by at least one camera in at least one first acquisition area and displayed on the display unit in a step;
  - c) at least one lighting field of interest with a corresponding brightness distribution is set via the operating unit in a step;
  - d) all lighting elements are switched off in a fourth step and each one of the plurality of lighting elements is switched on one after another in a sequence and an image is acquired by the at least one camera for every single lighting element and stored in a first data field;
  - e) the first data field is analyzed to determine if the at least one camera was hiding from view in a step;
  - f) the first data field is analyzed in a further step and the parameters for actuating the plurality of lighting elements are determined and stored in a first parameter field;
  - g) the individual lighting elements are switched by means of the control unit and a control view of the lighting is provided as output on the display unit in a step;

h) the actuation of the plurality of lighting elements is confirmed via the operating unit, the initialization is terminated and the operation is started in an eighth step;

i) a polling is performed in a further step to execute the first mode of operation for uniform lighting and the first mode of operation is continued;

j) the data image acquired by the at least first camera is analyzed in a continuous sequence in a further step and compared with the first data field and the actuation parameters of the first parameter field are adjusted; and k) the actuation by the control unit of the individual lighting elements of the lighting unit is performed in a further step according to the first parameter field and the first mode of operation is continued without interruption with a return to the step i).

12. A process in accordance with claim 11, wherein a polling is provided in the step i) for terminating the first mode of operation with uniform lighting.

13. A process in accordance with claim 11, wherein a polling is provided in the step i) for switching over into a second mode of operation.

14. A process in accordance with claim 11, wherein the actuation of the individual lighting elements of the lighting unit is carried out according to the second mode of operation.

15. A process in accordance with claim 11, wherein a first lighting field of interest and at least one second lighting field of interest are set via the operating unit.

16. A process in accordance with claim 11, wherein the switchover of the individual lighting elements takes place in a pulsed manner.

17. A process in accordance with claim 13, wherein the second mode of operation is a mode in which the maximum luminosity of all lighting elements is switched on.

18. A process in accordance with claim 13, wherein the second mode of operation is a mode based on an average brightness distribution of all lighting elements according to the first parameter field.

19. A process in accordance with claim 13, wherein the second mode of operation is a mode of manually preset luminosity of all lighting elements.

20. A device for uniformly lighting at least one lighting field, the device comprising:
    a lighting fixture housing;
    a lighting unit with a plurality of lighting elements accommodated in said lighting fixture housing, said plurality of lighting elements providing at least one lighting field area as output;
    a camera having a camera acquisition area, said camera providing data relating to image segments of said at least one lighting field area as output;
    an image processing unit receiving said output of said camera, said image processing unit analyzing said data such that said image processing unit determines light element actuation parameters of one or more of said lighting elements;
    a control unit providing one or more actuating signals to said one or more of said lighting elements, said control unit adjusting said one or more actuating signals in conformance with a relationship defined by said actuation parameters, wherein said one or more actuating signals reduce a difference in luminosity of said image segments, said control unit switching said plurality of lighting elements on one after another in a sequence to provide a plurality of switch-on events, said camera acquiring an image for each of said switch-on events of every single light element.

21. A process for operating a lighting system for uniformly lighting a lighting field, the process comprising the steps of:
    providing a plurality of lighting elements;
    switching the lighting elements on one after another in a sequence to provide a plurality of switch-on events;
    acquiring an image with at least one camera for each of said switch-on events of every single lighting element;
    storing each acquired image in a first data field;
    in a continuous sequence analyzing a data image acquired by the at least one camera and comparing the data image acquired with the first data field;
    providing a first parameter field comprising actuation parameters for controlling a luminosity of one or more of said lighting elements, said actuation parameters being determined based on said first data field;
    continuously adjusting actuation parameters of the first parameter field; and
    continuously adjusting individual lighting elements and the control unit continuously actuates the lighting unit according to the first parameter field, wherein said luminosity of said one or more of said lighting elements is continuously controlled by said control unit based on said actuation parameters.

22. A process in accordance with claim 21, wherein:
a) all lighting elements of the lighting unit are switched on simultaneously by the control unit in a step;
b) an image of the operating area is acquired by at least one camera in at least one first acquisition area and displayed on the display unit in a step;
c) at least one lighting field of interest with a corresponding brightness distribution is set via the operating unit in a step;
d) all lighting elements are switched off in a fourth step and each one of the plurality of lighting elements is switched on one after another in a sequence and an image is acquired by the at least one camera for every single lighting element and stored in a first data field;
e) the first data field is analyzed to determine if the at least one camera was hiding from view in a step;
f) the first data field is analyzed in a further step and the parameters for actuating the plurality of lighting elements are determined and stored in a first parameter field;
g) the individual lighting elements are switched by means of the control unit and a control view of the lighting is provided as output on the display unit in a step;
h) the actuation of the plurality of lighting elements is confirmed via the operating unit, the initialization is terminated and the operation is started in an eighth step;
i) a polling is performed in a further step to execute the first mode of operation for uniform lighting and the first mode of operation is continued;
j) the data image acquired by the at least first camera is analyzed in a continuous sequence in a further step and compared with the first data field and the actuation parameters of the first parameter field are adjusted; and
k) the actuation by the control unit of the individual lighting elements of the lighting unit is performed in a further step according to the first parameter field and the first mode of operation is continued without interruption with a return to the step i).

* * * * *